United States Patent [19]

Naser-Kolahzadeh et al.

[11] Patent Number: 5,492,837
[45] Date of Patent: Feb. 20, 1996

[54] MOUNTING MEDIUM FOR MICROSCOPE SLIDE PREPARATIONS

[75] Inventors: Zahra P. Naser-Kolahzadeh, Berkeley, Calif.; Joannis G. Stavrianopoulos, Bay Shore, N.Y.

[73] Assignee: Biogenex Laboratories, San Ramon, Calif.

[21] Appl. No.: 113,774

[22] Filed: Aug. 27, 1993

[51] Int. Cl.$^6$ .................................................... G01N 1/00
[52] U.S. Cl. .................... 436/176; 435/30; 435/40.52; 427/2.11
[58] Field of Search .................................. 436/8, 17, 18, 436/63, 176, 174; 424/3, 4; 435/4, 285, 30; 252/408

[56] References Cited

U.S. PATENT DOCUMENTS

| | | | |
|---|---|---|---|
| 3,498,860 | 3/1970 | Pickett | 156/308 |
| 3,852,155 | 12/1974 | Moore | 195/1.8 |
| 3,956,477 | 5/1976 | Price et al. | 424/8 |
| 4,219,334 | 8/1980 | Schluter et al. | 23/230 B |
| 4,587,222 | 5/1986 | Guffroy | 436/509 |
| 4,731,335 | 3/1988 | Brigati | 436/180 |
| 4,946,669 | 8/1990 | Siegfried et al. | 424/4 |
| 5,104,640 | 4/1992 | Stokes | 424/3 |

OTHER PUBLICATIONS

Jones et al., "Transition Metal Salts As Adjuncts To Formalin For Tissue Fixation" (1981) *Laboratory Investigation* volume (44):32A.

Fox et al., "Formaldehyde Fixation" (1985) *The Journal of Histochemistry and Cytochemistry* 33 (8):845–853.

Taylor et al., "Immunohistologic Techniques in Surgical Pathology—A Spectrum of New Special Stains" (1981) *Human Pathology* 12(7):590–596.

Herman et al., "Zinc Formalin Fixative For Automated Tissue Processing" (1988) *The Journal of Histotechnology* 11(2):85–88.

Battifora, H. and Kopinski, M., "The Influence of Protease Digestion and Duration of Fixation on the Immunostaining of Keratins—A Comparison of Formalin and Ethanol Fixation" (1986) *The Journal of Histochemistry and Cytochemistry* 34(8):1095–1100.

Hafiz et al., "Use of microwaves for acid and alcohol fast staining" (1985) *J Clin Pathol* 38:1073–1984.

*Primary Examiner*—David A. Redding
*Attorney, Agent, or Firm*—James C. Weseman; Gray Cary Ware & Freidenrich

[57] ABSTRACT

Aqueous polyvinylpyrrolidone (PVP) compositions and processes employing aqueous PVP, for use in mounting hematological, cytological and histological specimens on microscope slides.

5 Claims, No Drawings

MOUNTING MEDIUM FOR MICROSCOPE SLIDE PREPARATIONS

INTRODUCTION

1. Technical Field

The invention relates to media for mounting tissue samples, such as stained hematological, histological and cytological specimens, on microscope slides.

2. Background

Tissue sections and blood samples obtained from clinical specimens or animal experiments frequently are mounted, fixed and stored in a form suitable for examination by light microscopy. Mounting is the process by which the specimen is adhered to the microscope slide and protected from physical damage.

Traditional mounting media fall into two classes: resinous and aqueous. Resinous mounting media contain natural or synthetic solid resins that are dissolved in an appropriate organic solvent, typically toluene or xylene. First, the tissue to be mounted and preserved is dehydrated in alcohol. Since most synthetic resins in solution have an index of refraction in the range of 1.51 to 1.55 and tissues have an average index of refraction in the range of 1.53 to 1.55, such resinous solutions, standing alone, meet the essential requirements for utility as a mounting medium, clarity. However, if dehydration of the stained tissue sections is not complete, opaque or cloudy areas may appear and deleteriously affect viewing, despite the appropriate refractive indices. Accordingly, the specimen is cleared by immersion in xylene before being placed on a microscope slide and mounted by application of a few drops of the resinous mounting medium. The most widely used resinous medium is Permount™ (Fisher Scientific). Such resinous mounting materials are considered to be permanent.

Aqueous mounting media are typically made from simple syrups, gum arabic or glycerol gelatins. Because the refractive index of aqueous mounting media often differs significantly from that of the specimen, the level of clarity attainable using aqueous mounting media is generally not as high as the level of clarity attainable using resinous mounting media, particularly for microscopic evaluations using powers of 45X and up. For example, an aqueous commercial mounting composition is available that contains polyvinylalcohol, but this finished mount has a refractive index of 2.1. Additionally, most aqueous mounts are considered to be temporary, since the mounting medium can readily be dissolved with water or affected gradually over time by humidity. However, in comparison to resinous mounting media, aqueous mounting media do not require dehydration and clearing step using toxic components such as toluene or xylene. Each type of media therefore has its advantages and disadvantages: resinous media have a desirable refractive index and are permanent but very difficult to handle; existing aqueous media are safe and easy to handle but have an undesirable refractive index and are not permanent. It would be advantageous to find a new mounting medium that combines the advantages of resinous and aqueous media and eliminates their disadvantages. Applicant has found such a medium.

SUMMARY OF THE INVENTION

Accordingly, the present invention provides compositions and methods for permanently mounting tissue sections on microscope slides using an aqueous solution of polyvinylpyrrolidone. The microscope slides produced by this process are also part of the present invention. The mounting compositions of the invention are simple to use, merely requiring that the user apply from one to a few drops of polyvinylpyrrolidone aqueous solution to a tissue section on a microscope slide. The concentration of the solution can vary widely depending on the desires of user. Conversion of the aqueous solution into a permanent mount is accomplished by simple drying. The refractive index of the dried polyvinylpyrrolidone is ideal for most tissues, and the resulting hard, clear, plastic-like mount does not require the use of a coverslip.

DESCRIPTION OF SPECIFIC EMBODIMENTS

Surprisingly, it has been found that an aqueous solution of an already existing substance commonly used in the medical field as a carrier for drugs is a most appropriate medium for mounting tissue sections on slides for microscopic examination. Polyvinyl-pyrrolidone (PVP) is a known substance of low toxicity that is used as a thickener for pharmaceutical liquids and a carrier of drugs, such as iodine. Accordingly, it has desirable low toxicity for ease of handling and has further been found by the inventors to have other properties that make it suitable for use as a mounting medium. In the past PVP has been used as an additive to fixative liquids to help stabilize the cellular components of blood smears and histological specimens against variations in osmotic pressure. See for example, U.S. Pat. Nos. 5,104,640 and 4,946,669 disclosing PVP's use as a stabilizer in methanolic fixing solutions. In such case little if any PVP is present at the mounting step of slide preparation. PVP has not heretofore been used or suggested for use as a mounting medium. Nevertheless, PVP has the ability to function as a superb permanent mounting medium, a property not previously recognized in the art.

Accordingly to our invention, aqueous PVP is employed as a mounting medium for hematological, histological and cytological microscope slide preparations and for any other slide mounting situation involving tissue and blood preparations.

This newly recognized use of PVP provides the art with a permanent, aqueous-based mounting medium that conveniently eliminates the requirement of dehydrating and/or clearing the specimen prior to mounting that is necessary for organic-based media. The use of PVP also eliminates the requirement that coverslips be used to cover and protect the mounted specimen after staining, because PVP itself solidifies to a hardened, polymeric surface upon drying.

For use in the present invention, polyvinylpyrrolidone is dissolved in water. Since PVP is a polymer, it is generally available as a mixture of molecules of different lengths. Commercially prepared polyvinylpyrrolidone (e.g., from Sigma Chemical Co.) is generally sold as a composition having an average molecular weight in a defined range, depending on the process used by the manufacturer to make PVP and the needs of the particular user. For use in the present invention, the only limits on the molecular weight of polyvinylpyrrolidone are that it be soluble in water to an extent sufficient to allow use as described herein and that an aqueous solution of PVP dries to form a hard polymeric surface. The upper end of the molecular weight range that is useful is thus generally defined by the solubility of the composition, while the lower end of the range is generally defined by the ability of the dried polymer to form a hardened surface. Although careful drying and dissolution techniques can extend the range of useful molecular weights, commercially useful polyvinylpyrrolidone compositions are likely to have a minimum molecular weight above 40,000, preferably above 100,000, more preferably above 300,000, in order to form a sufficiently hard polymer. There are less constraints on the upper molecular weight limit, such limits principally resulting from manufacturing techniques for polyvinylpyrrolidone and by solubility. Typical molecular weights are under 1,000,000, with molecular weights under 500,000 being quite satisfactory and more readily available on a commercial basis.

In selecting a polyvinylpyrrolidone composition for use in a mounting medium of the invention, the molecular weight is also selected to provide a refractive index in the desired range. As previously discussed, most tissues have a refractive index in the range 1.53 to 1.55, and mounting media having a refractive index less than or equal to that of the tissue being mounted are preferred. Since the PVP used in this invention will generally be obtained from a commercial supplier and since the distribution of molecules of a given length affects the refractive index, a source of PVP is preferably selected by empirical testing so that the dried mount has a refractive index of 1.55 or less.

The concentration of polyvinylpyrrolidone in the aqueous solution of the invention can vary widely, and there are no known limits other than the solubility limit of the polymer. However, very dilute solutions contain only a small amount of the polymer and thus may not deposit sufficient polymer when dried unless several applications of the aqueous solution to the tissue are made during the mounting process. Since processes that require multiple applications of mounting solution are undesirable, solutions containing at least 1% PVP are generally used, preferably at least 3%, and more preferably at least 5 %. At the upper end of the concentration range, concentrated solutions are viscous and difficult to use, although they can be used with careful handling. For ease of operation, solutions containing less than 25% PVP are desirable, preferably less than 15%, and more preferably 10% or less.

Throughout this application, percentages of solids dissolved in liquids represent weight per unit volume (w/v). Accordingly, a 10% solution of PVP and water contains 10 grams of PVP in a 100 milliliter solution at room temperature (normally considered to be 20° C.).

The aqueous solution containing the polyvinylpyrrolidone need not contain any components other than the water solvent. In order to prepare the aqueous solution, i.e., to dissolve the PVP, it is often necessary to apply heat at 50°–70° C., preferably 60°–65° C. Additionally, since polyvinylpyrrolidone is susceptible to degradation by bacterial and other microbial attack during storage, a preservative is generally included in solutions that are intended to have a long shelf life. Since the preservatives are generally present in small amounts, there are no particular limits on the preservative used. However, it is desirable that the preservative not absorb a significant amount of light in the visible light range so that the preservative will not interfere with visual examination of the mounted slide. Any of the preservatives commonly used as anti-microbials can be used in the present invention, such as sodium benzoate or sodium azide. Sodium azide is a particularly preferred preservative. The preservative is normally present at a concentration of less than 2%, more usually less than 1%, and often is present at a fraction of a percent.

Mounting a tissue sample on a microscope slide is a well known and easily carried out process, and the present invention requires no modifications. None of the preliminary steps, such as preparation, fixing or staining of a tissue section, is part of the present invention. Those readers who would like examples of these earlier steps of the overall slide-preparation process are referred to any of the numerous texts and teaching manuals in this field, such as Carson, F., *Histotechnology, a Self Instructional Text*, ASCP Press, Chicago, 1990 (especially pages 112–114, 159–160 and 231–248); Lillie, P., *Histopathologic Technique and Practical Histochemistry*, 2nd Ed., McGraw-Hill, New York, 1954 (especially page 303); and Taylor, C., and Kledzik, G., "Immunohistologic techniques in surgical pathology—a spectrum of "new" special stains," *Hum. Pathol.* 12:590–596 (1990).

Instead, the composition of the invention is used, and the method of the invention begins, when the tissue (sectioned or unsectioned, fixed or unfixed) is being mounted on a microscope slide. Here "tissue" refers either to part or all of an organ tissue or a sample of a fluid, such as blood or sputum, from the body of a plant or animal, including even a single cell (especially a human tissue). The process is quite simple, consisting of contacting a tissue adhered to a microscope slide with an aqueous solution of polyvinylpyrrolidone having a composition as described herein, and drying the slide to remove excess water so that the polyvinylpyrrolidone solidifies. The amount of mounting composition to use is determined by the user and generally is just sufficient to thoroughly wet the surface of tissue. Excess mounting solution can be removed if desired, such as by blotting or (more commonly) tilting the slide in order to allow excess fluid to drain off the slide. Application of the mounting composition to the tissue on the slide is commonly carded out by using a dropper and applying one to several drops of the mounting composition to the tissue as it rests on the microscope slide.

The only remaining step in the method of the invention is the drying of the slide to remove excess water. Drying can be carried out in any conventional manner, either with or without the application of heat. Although the solution will evidently dry at room temperature, the slide is preferably dried at an elevated temperature, typically in the range of 60°–90° C., more typically at about 80°–85° C. Drying can take place in the presence of conditions intended to remove moisture more rapidly, such as by employing a vacuum pump or a desiccant, or these additional drying procedures can be absent. Whether sufficient mounting composition was added initially can readily be determined after drying from the appearance of the mounted tissue. If sufficient PVP is present, the tissue will be firmly attached to the slide by the PVP and sufficient PVP will be present on the exposed surface of the tissue to protect the tissue from abrasion. If necessary, additional mounting composition can be added, and the drying process can be repeated.

The resulting mounted tissue on the microscope slide comprises the transparent base member (i.e., the microscope slide itself), the tissue section, and solidified polyvinylpyrrolidone surrounding the tissue and adhering to the tissue section and to the base member. If desired, a coverslip can be positioned over the tissue section while the polyvinylpyrrolidone solution is fluid and will further protect the tissue sample once the PVP solidifies. PVP adheres readily to both glass and plastic surfaces and can be used with any of the transparent tissue materials (usually glass or an organic polymer) that are used in the preparation of mounted microscope slides. See, for example, any catalogue from a supplier of microscope slides, such as Fisher Scientific (Pittsburgh, Pa.; e.g., 1988 general catalogue, pages 708–714). A coverslip can also be attached by other standard techniques, such as by use of a second adhesive or mounting material after the PVP composition has solidified.

The amount of solidified polyvinylpyrrolidone present on the mounted slide is sufficient when the polyvinylpyrrolidone surrounds the tissue, and, if desired as discussed above, so that the tissue adheres via the solidified polyvinylpyrrolidone to the transparent base member and/or, if present, the coverslip. There is no maximum amount of solidified PVP, other than for economic and practical considerations. A typical weight ratio of prepared tissue section to polyvinylpyrrolidone is in the range of from 1:200 to 2:1, preferably 1:100 to 1:1, and more preferably 50:1 to 1:2, especially about 30:1.

The invention now being generally described, the same will be better understood by reference to the following detailed examples, which are provided for illustration only and are not to be considered limiting of the invention.

EXAMPLE

Mounting Procedure Using PVP Compositions

A particularly preferred mounting medium contained 7.5 % (w/v) polyvinylpyrrolidone having an average molecular weight of 360,000 (Sigma Chemical Co.) in a water solution that also contained 0.1% (w/v) sodium azide as a preservative. This mounting medium was usually applied while slides were still wet. Generally, 1–3 drops of this medium were applied to the tissue section, and the slides were tilted so that the tissue section was full, covered. The excess medium was allowed to drip off the side while the slide was held a a vertical position.

The thin coating of polymer on the slide hardened at varying times for different temperatures ranging from room temperature to 85° C. The solidification of the polymer at room temperature was accomplished in less than 1 hr, and the same result at 65° C. was obtained in 5–8 minutes.

Once the polymer hardened, the slides could be microscopically examined without requiring any coverslips; however if application of a coverslip was desired the slides could be coverslipped by use of any adhesive agent, such as clear nail polish, an aqueous mounting medium, or a resinous organic-solvent-based mounting medium such as Permount™. If Permount™ was used as the adhesive agent for a coverslip in conjunction with the PVP as the mounting medium, no chemical pre-treatment in organic solvents, such as dehydrating in alcohol or clearing in xylene, was necessary. Permount™ was directly applied onto the hardened polymer surface and coverslipped.

Post-mounting with another mounting medium for the application of a coverslip could be eliminated since PVP can be directly applied for its adhesive properties. If this procedure is to be followed, it is recommended that the PVP solution be warmed to 60° C. for 2 min prior to use in order to minimize the formation of air bubbles. In some cases a coverslip was directly applied over the slide-mounted specimen after application of the PVP mounting medium and before the PVP mounting medium solidifies in the manner just described.

The mounting medium of the invention was successfully used to provide a permanent mount for tissues stained with a number of stains (such as Fast Red™ and a number of fluorescent stains, such as phycoerythfin or its related derivatives such as allophycocyanin, phycocyanin, and fiuoroBlue) that cannot be readily used with organic-based permanent mounting compositions. The preservation of slide-mounted tissue sections stained with these fluorescent stains has previously only been carried out with non-permanent aqueous mounts because of the sensitivity of these materials to organic solvents.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. A method of mounting a tissue on a slide and examination with a microscope, which comprises:

applying a tissue to a slide;

contacting said tissue on said slide with an aqueous solution of polyvinylpyrrolidone having an average molecular weight of greater than 40,000;

drying said slide to remove excess water, whereby said polyvinylpyrrolidone solidifies; and microscopic examination of said tissue on said slide without prior dissolution of said, solidified polyvinylpyrrolidone.

2. The method of claim 1, wherein said tissue is fixed prior to said contacting wit said aqueous solution.

3. The method of claim 1, wherein said solution contains 3–15 % (w/v) polyvinylpyrrolidone.

4. The method of claim 1, wherein said drying occurs at a temperature from 60 to 90 degrees celsius.

5. The method of claim 1 further comprising a step of placing a coverslip on said tissue while said polyvinylpyrrolidone solution is fluid.

* * * * *